United States Patent
Guo et al.

(10) Patent No.: US 9,931,440 B2
(45) Date of Patent: Apr. 3, 2018

(54) BIOCOMPATIBLE SELF-LUBRICATING POLYMER COMPOSITIONS AND THEIR USE IN MEDICAL AND SURGICAL DEVICES

(71) Applicant: St. Jude Medical, Atrial Fibrillation Division, Inc., St. Paul, MN (US)

(72) Inventors: Xiaoping Guo, Eden Prairie, MN (US); Richard E. Stehr, Tuscon, AZ (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

(21) Appl. No.: 15/594,165

(22) Filed: May 12, 2017

(65) Prior Publication Data

US 2017/0312396 A1    Nov. 2, 2017

Related U.S. Application Data

(63) Continuation of application No. 11/482,814, filed on Jul. 10, 2006, now abandoned.

(60) Provisional application No. 60/795,593, filed on Apr. 28, 2006.

(51) Int. Cl.
| | | |
|---|---|---|
| A61K 8/72 | (2006.01) | |
| A61L 29/04 | (2006.01) | |
| A61M 25/00 | (2006.01) | |

(52) U.S. Cl.
CPC ............ *A61L 29/049* (2013.01); *A61M 25/00* (2013.01); *A61M 25/0021* (2013.01); *A61M 2025/006* (2013.01); *A61M 2025/0048* (2013.01); *A61M 2025/0062* (2013.01)

(58) Field of Classification Search
None
See application file for complete search history.

(56) References Cited

U.S. PATENT DOCUMENTS

| | | | |
|---|---|---|---|
| 3,449,290 A | 6/1969 | Foster et al. | |
| 4,438,007 A | 3/1984 | Snyder, Jr. et al. | |
| 5,208,293 A | 5/1993 | Oki et al. | |
| 5,562,632 A | 10/1996 | Davila et al. | |
| 5,782,817 A | 7/1998 | Franzel et al. | |
| 5,807,350 A | 9/1998 | Diaz | |
| 5,945,498 A | 8/1999 | Höpken et al. | |
| 6,280,765 B1 | 8/2001 | Gueret | |
| 6,551,283 B1 | 4/2003 | Guo et al. | |
| 6,632,200 B2 | 10/2003 | Guo et al. | |
| 6,702,255 B2 | 3/2004 | Dehdashtian | |
| 6,723,073 B2 | 4/2004 | Ley et al. | |
| 6,776,774 B2 | 8/2004 | Tansy, Jr. et al. | |
| 2001/0012861 A1 | 8/2001 | Liu | |
| 2004/0148007 A1 | 7/2004 | Jackson et al. | |
| 2005/0142315 A1 | 6/2005 | DeSimone et al. | |
| 2005/0165357 A1 | 7/2005 | McGuckin, Jr. et al. | |
| 2005/0192537 A1 | 9/2005 | Osborne et al. | |
| 2005/0212222 A1 | 9/2005 | Tachikawa et al. | |
| 2005/0232807 A1 | 10/2005 | Nishimura | |
| 2005/0273146 A1 | 12/2005 | DeSimone et al. | |
| 2005/0288701 A1 | 12/2005 | Quinn et al. | |

FOREIGN PATENT DOCUMENTS

| | | |
|---|---|---|
| EP | 1092747 | 4/2001 |
| WO | 01/05882 | 10/1996 |

OTHER PUBLICATIONS

J. Letey et al., Wetting Agents, Can Increase Water Infiltration or Retard it, Depending on Soil Conditions and Water Contact Angle, California Agriculture, pp. 8-9, Oct. 1961.
Silastic BioMedical Grade ETR Elastomers (Q7-4720, Q7-4735, Q7-4750, Q7-4765, Q7-4780) Parts A & B, p. 6, Aug. 2005.
Saito et al., Usefulness of Hydrophilic Coating on Arterial Sheath Introducer in Transradial Coronary Intervention, Catheter Cardiovasc. Interv. 56(3):323-332, Jul. 2002, (Abstract).
Ikada et al., Lubricating Polymer Surfaces, Technomic Publishing, pp. 1-70, 139-163, (1993).
International Search Report and Written Opinion for PCT/US07/67407 dated Sep. 18, 2008.

*Primary Examiner* — James W Rogers
(74) *Attorney, Agent, or Firm* — Wiley Rein LLP

(57) ABSTRACT

The invention comprises self-lubricating polymer compositions that are especially useful in medical devices and valves and gaskets of medical devices. In a preferred embodiment, the polymer compositions comprise a thermosetting or thermoplastic silicone elastomer in combination with a lubricity enhancing polyfluoropolyether fluid or hydrocarbon-based synthetic oil. In other preferred embodiments, the polymer compositions contain only biocompatible components. The improved anti-friction properties of the self-lubricating polymers can be demonstrated over a course of insertion and withdrawal cycles, where conventional polymers have changing and mostly increasing force required for each insertion and withdrawal, while the polymer compositions of the invention remain stable.

7 Claims, 5 Drawing Sheets

BIOCOMPATIBLE SELF-LUBRICATING POLYMER COMPOSITIONS AND THEIR USE IN MEDICAL AND SURGICAL DEVICES

CROSS-REFERENCE TO RELATED APPLICATIONS

This application is a continuation of U.S. application Ser. No. 11/482,814, filed 10 Jul. 2006, now pending, which claims the benefit of U.S. provisional application No. 60/795,593, filed 28 Apr. 2006. This application is also related to international application no. PCT/US07/67407. The foregoing are hereby incorporated by reference as though fully set forth herein.

FIELD OF THE INVENTION

The invention relates to polymer compositions with enhanced anti-friction properties for use in medical applications and medical devices. The polymer compositions have reduced friction characteristics and can be implemented in tubing, gaskets, valves, and in a variety of insertion devices and other devices used in procedures to introduce objects into the body, for example.

BACKGROUND

A growing number of surgical or medical procedures employ devices and kits that rely on inserting a device or tube through a sealed valve or apparatus. For example, catheters and guides are typically inserted through a sterile valve to introduce fluids, intraluminal devices and many other instruments into the body or into the lumen of a blood vessel. In fact, various surgical kits now include valves and devices to assist in the simultaneous, sterile insertion of multiple elements into vessels or elsewhere in the body. To operate properly, the valves must be capable of accepting different sized elements, be sufficiently pliable and/or elastic to maintain a seal during manipulation, and allow the user to effectively introduce and remove devices under sufficient control to avoid damage to vessels or other body tissue. However, pliable or flexible polymers tend to cause a degree of friction when an element is inserted or withdrawn into or through them. During medical or surgical procedures, this friction is undesirable and may lead to a lack of control and require forceful insertion or withdrawal. Some kits and procedures even require multiple guidewire and catheter exchange steps, for example, which exacerbates the insertion and withdrawal problems. The sealed or sealable valves used must also prevent the introduction of air into a blood vessel and/or contamination of body tissue during insertion and withdrawal. Because of these and other requirements, the safe insertion and withdrawal, as well as the related forces used to insert and withdraw, has become a problem with many devices and kits used today. To attempt to alleviate this problem, silicone oil is customarily used to externally lubricate the valves and devices. During a medical procedure, this lubricant can be wiped away or lose its effectiveness after even a single insertion and withdrawal action.

A high performance hemostasis valve has recently been described that can be sealed effectively to prevent leaks and contamination and which is capable of accepting various catheters having a variety of diameters (see, for example, U.S. Pat. No. 6,632,200). As described below, the inventors' improvements on this and many other devices, which in part addresses the friction problem during insertion and withdrawal noted above, includes a self-lubricating polymer composition that effectively allows elements to slide in and out of valves, other devices, tubes, or through tissue in a more controlled and easier manner. Accordingly, the use of the self-lubricating polymer compositions of the invention improves the performance and use of a variety of medical and surgical devices and kits. In addition, the polymer compositions can be used to improve basic catheter and tubing applications, or wherever one material slides over or across another material in a sealed or sealable device, valve, or gasket.

BRIEF SUMMARY

In one aspect, the invention addresses the use of a self-lubricating polymer composition to make at least a part of or element to a medical or surgical device, or a kit comprising such medical or surgical devices. In some applications, it is desirable for these polymers to be flexible enough to form a sufficient seal around the surface of any element inserted into it and/or in contact with it during the course of using the device. For example, the self-lubricating polymer can be used as a gasket at or around the insertion site of a guide or catheter. Similarly, the guide or catheter itself can be made of, or at least partially made of, the self-lubricating polymer.

In a general aspect, the invention addresses the use of a polymer material at a semidynamic seal, such as where one part moves along, slides over, or contacts another part or element in the practice or use of a medical or surgical device, and/or at a dynamic seal, where two or more parts similarly contact or move against each other. Various gaskets, valves, covers and other sealing structures can be used in medical and surgical devices to produce a semidynamic or dynamic seal. Thus, any of the existing and/or future sealing structures can be improved through the use of the polymer compositions of the invention.

In another general aspect, the invention provides self-lubricating or enhanced lubricity polymer compositions for use in medical and surgical devices and related applications. The term lubricity is used in the conventional sense of a lubricating characteristic that effectively reduces friction between rubbing or contact surfaces. Lubricity can be most important in conditions of boundary lubrication and/or for continuously maintaining a low surface-energy and/or to effectively repel body fluids and the resulting drag forces on contact surfaces. By increasing the lubricity of the polymer material used, the degree of deformation can be limited for a particular structure to form or maintain a leak-proof seal, while the force needed to slide over or through the structure is reduced. A preferred example of a self-lubricating polymer composition comprises a biocompatible elastomer, and especially preferred is a biocompatible silicone elastomer. Other biocompatible blends of elastomers and/or thermoplastic polymers can also be used, as known in the art. The self-lubricating compositions also comprise one or more lubricants, such as synthetic oils and/or solid lubricants. Preferred synthetic oil lubricants are polyfluoropolyether (PFPE) synthetic oils, and hydrocarbon-based synthetic oils, namely co-oligomers of ethylene and olefins. Preferred solid lubricants include low molecular weight polytetrafluoroethylene powders, titanium dioxide micropowders, molybdenum disulfide micropowders, graphite micropowders or flakes, and baron nitride micropowders and the like. Any combination of these lubricants and others available and/or used in the art for biocompatible materials can be selected, and preferred combinations are given in the Examples.

As noted above, the self-lubricating polymer compositions can be used to produce one or more parts or elements in a medical or surgical device. In one preferred example, the part or element can comprise all or part of an insertion device or a receiving area for an inserted device or other elongated medical device. Typically, a receiving area employs a gasket or seal, which can readily and/or repeatedly permit passage of one or more devices, optionally of varying diameters. The gasket or seal or other receiving area is comprised of the polymer composition of the invention and thus has improved lubricity characteristics, for example with respect to a reduction in insertion and withdrawal forces compared to other materials and/or a reduction in the fluctuation of frictional forces during repeated or regular use. The receiving area can also be or comprise a centering orifice for inserting a device, which functions to position or center the inserted device into a particular region. Furthermore, multilayered structures may also be used, wherein at least one layer comprises a self-lubricating composition of the invention, preferably a layer in contact with another component or against which frictional forces are generated during use. In a preferred example, the outer layer of an inserting device and/or the inner layer of a receiving area, such as a gasket, sheath or seal, comprises a biocompatible self-lubricating composition of the invention. In addition, various lengths of the inserting device or receiving area can comprise a self-lubricating polymer composition of the invention, anywhere from the entire insertion length, to less than 10% of the insertion length, to only the tip or inserting end of the insertion device, and even intermittent or non-contiguous sections covering a desired percentage of the insertion length can be used. Thus, a multilayered tube or sheath can be made and used, and one of skill in the art is familiar with molding and co-extrusion processes, for example, for producing these parts of medical devices.

Accordingly, it is one object of the invention to provide a medical or surgical device that comprises a receiving area and/or insertion device made at least in part of a self-lubricating polymer composition. The parts, elements, biomedical, medical or surgical devices that contain the receiving areas or comprise insertion devices can thus exhibit improved anti-friction performance in the ease with which insertion and withdrawal of elongated elements or parts occurs and in the maintenance of adequate sealing characteristics to avoid or substantially avoid leakage of fluids, blood, or the flow of air during use. It is an additional object to provide a biocompatible polymer for use in biomedical applications, including human, veterinary, and biomedical research fields, wherein a self-lubricating polymer of the invention provides an improved lubricity surface for inserting into or withdrawing from or out of a variety of devices or body tissues.

Other objects, features, details, utilities, and advantages of the present invention will be apparent from the following more particular written description of various embodiments and examples of the invention, as further illustrated in the accompanying drawings and defined in the appended claims.

DETAILED DESCRIPTION

Figure 1:
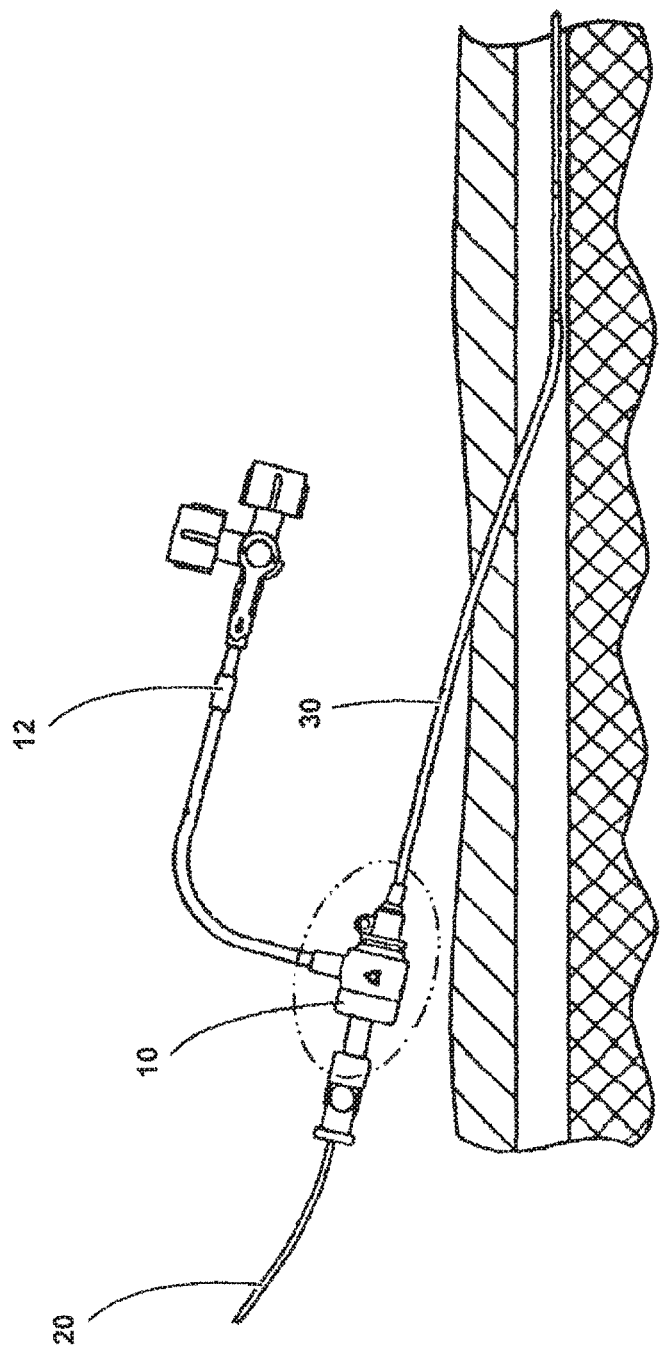
FIG. 1 depicts a cross-sectional view of preferred cardiac catheter device comprising hub 10 containing a hemostasis valve as exemplary receiving area, a stopcock assembly 12, a guidewire 20, and a catheter sheath or shaft 30 extending into the lumen of a vessel. The valve receiving area comprises a gasket or seal made of a self-lubricating polymer of the invention primarily comprising a silicone elastomer and a synthetic oil. The forces required to introduce, manipulate, control, and/or withdraw the catheter device are substantially less than those when a conventional elastomer without modification is used for the gasket or seal.
Figure 2:
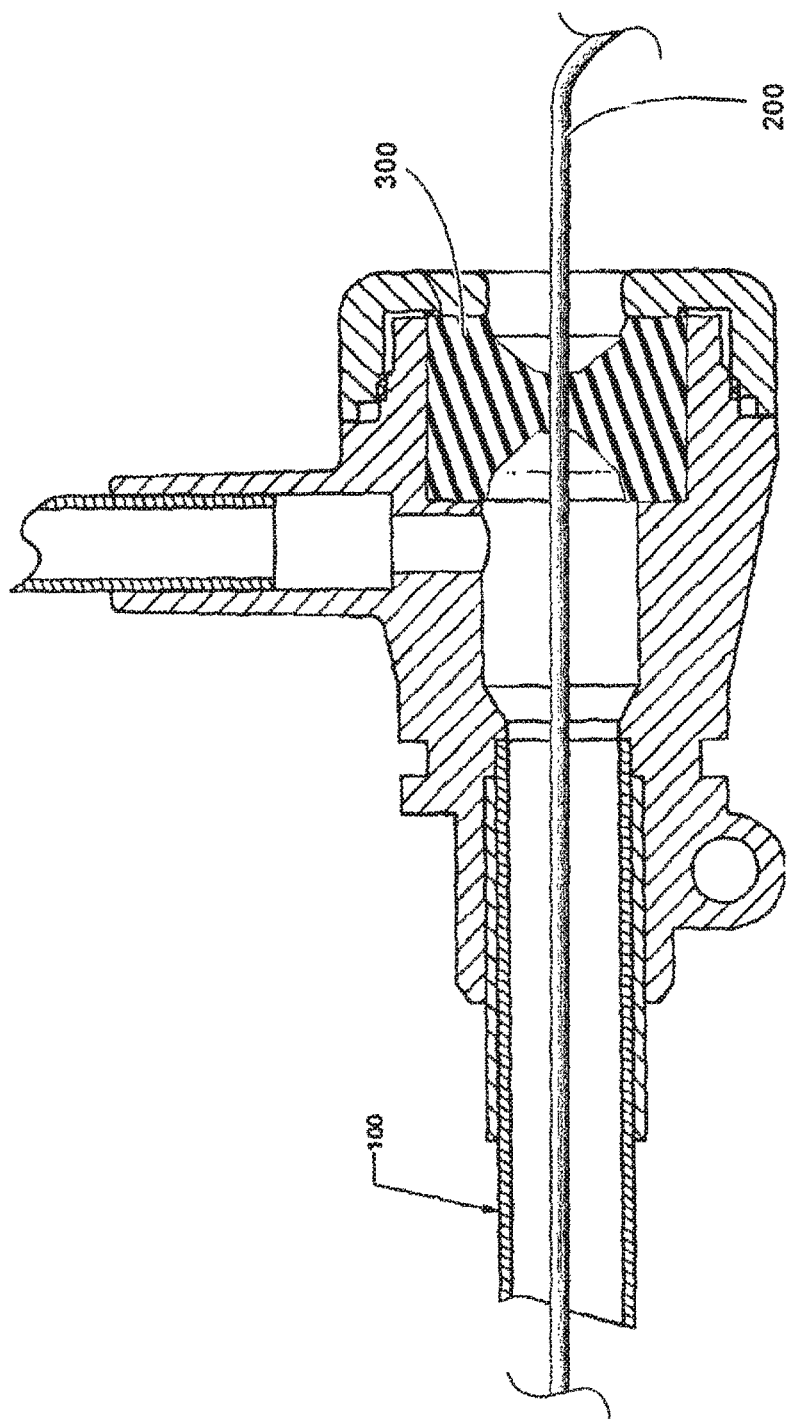
FIG. 2 depicts a close-up, cross-sectional view of an inserting device 200 inserted into a hemostasis valve, where various parts or elements of the valve can be made of the self-lubricating polymer of the invention. For example, sheath 100 (on its inner and/or outer surface) and gasket area 200 can both be composed of the self-lubricating polymer compositions of the invention to improve performance, such as anti-friction and sealing performance.
Figure 3:
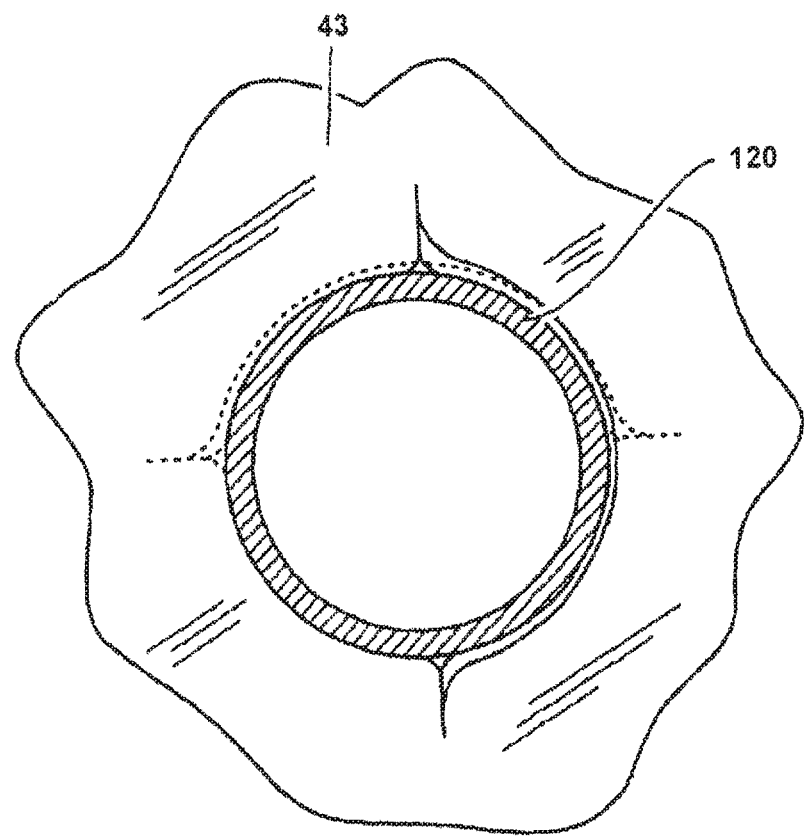
FIG. 3 is a radial, cross-sectional view of a catheter sheath or shaft 120 passing through the gasket 43 of a valve, for example, similarly, any tubing used in or inserted into a body tissue can be made of a self-lubricating polymer composition of the invention.

Throughout this disclosure, applicants refer to texts, patent documents, and other sources of information. One skilled in the art can use the entire contents of any of the cited sources of information to make and use aspects of this invention. Each and every cited source of information is specifically incorporated herein by reference in its entirety. Portions of these sources may be included in this document as allowed or required. However, the meaning of any term or phrase specifically defined or explained in this disclosure shall not be modified by the content of any of the sources.

The headings (such as "Introduction" and "Brief Summary") used are intended only for general organization of topics within the disclosure of the invention and are not intended to limit the disclosure of the invention or any aspect of it. In particular, subject matter disclosed in the "Introduction" includes aspects of technology within the scope of the invention and thus may not constitute background art. Subject matter disclosed in the "Brief Summary" is not an exhaustive or complete disclosure of the entire scope of the invention or any particular embodiment.

As used herein, the words "preferred," "preferentially," and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the invention and no disclaimer of other embodiments should be inferred from the discussion of a preferred embodiment or a figure showing a preferred embodiment. In fact, the nature of the polymer compositions of the invention allow one of skill in the art to make and use the invention on any medical or surgical device available or contemplated.

The phrases "self-lubricating polymer composition," "self-lubricating composition," and "polymer composition of the invention" all refer to a composition comprising a biocompatible polymer or blend of polymers and a biocompatible lubricant. In preferred embodiments, the composition is composed of polymer compounds that have not previously been used together, or in a particular ratio or ratios, for use in a medical, surgical, or biomedical device.

The invention relates to the new, successful development of various self-lubricating polymer compositions, and especially silicone elastomer compositions, which can be used to make a variety of medical and surgical devices and thereby minimize friction forces during use while maintaining sufficient sealing characteristics. In one aspect, particular surfaces or elements of devices comprise a self-lubricating polymer of the invention. The medical devices of preferred interest include, but are not limited to, hemostasis valves of a variety of types including those for cardiac catheters, medical tubing, sheaths and gaskets used in valves and insertion devices, ultrasound catheters, and similar devices.

In one general sense and without any intention to limit the scope to any particular explanation or mechanism for how it works, the invention provides a lubrication system for a polymer material, preferably a silicone elastomer material, through physical modifications of the polymer matrix. Parts or components of a medical device can thus be made to exhibit an improved surface lubricity and result in low friction forces during use or in medical procedures, providing advantages by at least improving the ease of use and/or comfort to a patient. Thus, it is one object of this invention to provide a self-lubrication mechanism for a surface or polymer matrix, such as a silicone elastomer matrix, such that any medical or surgical device made from the polymer matrix can release or spontaneously release embedded lubricant from the matrix or onto a contact surface(s) when the device is used. Accordingly, contact surface lubricity and the resulting lowered frictional forces during use can be reliably maintained throughout a procedure. Another object is to provide a lubrication system for a silicone elastomer that is biocompatible and can be used with a variety of medical and surgical devices and parts or elements thereof. Further, the lubrication and anti-friction performance characteristics are not degraded but can actually be enhanced by contact with blood, tissue, or medical fluids.

In preferred embodiments, the polymer compositions of the invention are designed to act like a matrix that allows the lubricant contained within to continuously migrate to the surface of the part or device made of the polymer. In effect, the lubricant is driven to the surface as the friction forces of the insertion and withdrawal cycles move the lubricant or wipe the lubricant away. After manufacture, the surface of the polymer composition is essentially primed with lubricant. As this lubricant is used during insertion and withdrawal cycles, the lubricant in the matrix migrates to replace the surface lubricant. The result is a constant friction force throughout the insertion and withdrawal cycles. Any of the polymer resins discussed here or in the Examples can form an effective matrix for migration of lubricant. In addition, solid porous silica powder or similar powders can optionally be added to increase the amount of lubricant contained in the matrix.

A number of polymers have been suggested as self-lubricating in a variety of applications, including: polyethylene; polyetherimide; polypropylene; polyetheretherketone (PEEK); polytetrafluoroethylene (PTFE) or Teflon (DuPont, Wilmington, Del.); Ultra High Molecular Weight (UHMW) polyethylene; polyoxymethylene or Delrin (DuPont, Wilmington, Del.); polyamide-imide (PAI) or TORLON (Solvay Advance Polymers, Alpharetta, Ga.); polyoxymethylene (POM), acetal resin, or Delrin (DuPont, Wilmington, Del.); and polyvinylidene fluoride or Kynar (Atochem Corporation). Some of these polymers do not possess the combination of flexibility and lubricity desired for the medical and surgical device applications noted herein. However, these polymers may be modified with similar methods of the invention and used to produce catheters and sheaths, for example, having improved anti-friction properties. Furthermore, the preferred polymer compositions of this invention are biocompatible, such as biocompatible thermosetting silicone elastomers and thermoplastic silicone elastomers.

In designing or selecting an acceptable or optimum polymer or blend of polymers for a particular device or part thereof, a method of the invention can take into account the matrix-controlled lubricant release mechanism. To optimize this mechanism or make it effective for a particular use, one can modify raw polymer compositions. In one example, a silicone elastomer resin can be cured with either organic peroxide crosslinking or, especially, by addition of a curing agent such as silicon hydride (SiH) and platinum as catalyst. In the latter approach, one can use liquid and/or solid lubricants, and preferably lubricants that are highly non-polar and chemically inert. The chemical inert characteristics can be important in avoiding combinations that interfere with a curing agent. The lubricants can also have low surface energies that are compatible with the polymer or blends used and, in the case of the silicone elastomers, can be about 20 mN/m (or dyne/cm). One or more lubricants with surface energies below 20 dyne/cm can be selected for use, as explained below and in the Examples. Furthermore, the percentage of lubricant used and the amount available during the insertion and withdrawal use can be changed to arrive at a desirable level for the anti-friction function for a particular part or medical device or method contemplated. One of skill in the art is familiar with varying the amount of lubricants and with additional compounds or additives, such as porous silica powders and the like, for increasing the amount of lubricant that can effectively create an anti-friction polymer composition or material.

In one method of producing the polymer compositions of the invention, the one or more lubricants are incorporated into the raw polymer or blend, such as the raw, gum-like silicone elastomer resin, with a two-roller mill compounding process as known in the art. After sufficient compounding to thoroughly mix the components, the lubricants are well dispersed into the matrix or occupy molecular pores within the matrix. To make a medical device part or element, the compounded polymer composition is molded, extruded or shaped and cured. In the case of a silicone elastomer, it is molded into shape and thermally cured. The curing process will create elastomeric, chemical crosslinks, which effectively trap the one or more lubricants in the polymer matrix. One can also consider the water repellency of non-polar lubricants and a lubricant concentration gradient from the center to the surface of the part. The limited chemical compatibility between the non-polar silicone elastomer and the non-polar lubricants, for example, can synergistically control the release of the lubricants to the surface. One of skill in the art is familiar with methods to produce concentration gradients.

Since silicone elastomers are one of the commonly used biomaterials in the medical device industry, the examples here and the preferred embodiments include silicone elastomers. However, the invention is not limited to the use of silicone elastomers or any particular polymer for that matter.

Silicone elastomers possess high coefficients of friction and relatively lack lubricity characteristics, which leads to patient discomfort and potential tissue trauma during medical procedures. The high friction forces generated during the insertion and withdrawal of catheters through an introducer containing a silicone elastomer, such as a hemostasis valve, have routinely challenged the medical devices industry. In practice, a hemostasis valve is externally lubricated with silicone oil during manufacture. During use, silicone oil is quickly removed by the insertion and withdrawal actions and, therefore, the lubricating effect from the silicone oil is quickly lost. As a result, the frictional forces are extremely inconsistent during a medical procedure and begin to vary from the first insertion. At the beginning of a procedure, the friction forces are relatively low due to the effect of the externally added silicone oil, while in the midst of a procedure the forces jump to an extremely high level as the oil dissipates, is removed or rubbed off. This can influence the physician's use and control of the device.

In the past, the industry has attempted to modify either hemostasis valve design (such as in various design found in U.S. Pat. Nos. 6,776,774; 6,723,073; 6,702,255; 6,632,200; 5,807,350; and 5,782,817) or the silicone elastomer materials by adding so-called solid lubricity enhancing additives, including bismuth oxychloride, PTFE powder, titanium dioxide, graphite, (see for example U.S. Pat. No. 5,562,632). Despite these attempts, none of hemostasis valves on the market provide constant performance and low friction forces.

As a preferred example of the improvements possible under this invention, the performance of hemostasis valve as shown in U.S. Pat. Nos. 6,632,200 and 6,551,283 can be improved by incorporating the self-lubricating polymer composition at various parts. A silicone elastomer is selected as well as liquid lubricants and/or solid lubricant additives. The liquid lubricants have low surface energies compared to the silicone elastomer or blend selected and this better ensures the partial solubility and compatibility of the liquid lubricant into the matrix of the silicone elastomer. By adjusting the lubricant used based upon the surface energy, an optimum release characteristic from the resulting cured polymer matrix and/or a controllable release rate can be found. For example, incorporating a solid lubricant or additional solid lubricant enhances the surface abrasive resistance, surface smoothness, and/or tear strength. Preferred liquid lubricants are polyfluoropolyether synthetic oils and hydrocarbon-based synthetic oils, while preferred solid lubricants are low molecular weight polytetrafluoroethylene powders, titanium dioxide, and baron nitrides. Both the liquid and solid lubricants are preferably chemically inert, devoid of chemical reactivity for the polymer or blend and curing agent used, and are preferably non-polar. This prevents them from interfering in the curing process. To increase the incorporation of a high or sufficient amount of synthetic oils or lubricants into the polymer matrix, a porous filler, such as porous silica, can optionally be added.

Generally, the self-lubricating polymer compositions of silicone elastomers contain 0.1 to 20 phr (part Per Hundredth Resin by weight) liquid lubricants and/or 0 to 20 phr solid lubricants. However, various preferred ranges of liquid and/or solid lubricant concentrations can be selected for use, including 1-20 phr, 1-5 phr, 3-5 phr, 3-6 phr, 4-6 phr, 3-10 phr, 1-10 phr, 1-15 phr, 5-15 phr, 8-10 phr, 10-20 phr, 15-20, and 5-10 phr, for example, can be used for either or both of the solid and liquid lubricant, alone or in combination. By selecting a fluid-like lubricant that has similar surface energy to that of the cured silicone elastomer but is chemically-inert, one of skill in the art can be better assured that the lubricant can be effectively contained in the molecular pores of the cured matrix due to surface tension. At the same time, the lubricants do not interfere with the chemical reaction of curing. Therefore, after curing, the fluid-like lubricant can be released under friction forces, preferably with continuous migration driven by the concentration gradient existing from the bulk material to the surface.

The following are some examples of the preferred self-lubricating polymers of silicone elastomers of the invention in which polyfluoropolyether (PFPE) or perfluoroalkylether synthetic oil (having surface energies of 18 to 20 mN/m or dyne/cm) are used as liquid lubricants. In addition or alternatively, boron nitride or low molecular weight polytetrafluoroethylene (PTFE) micropowders may be used as solid lubricants to adjust anti-friction or abrasion resistance and/or tear strength.

A preferred example of a medical device or part thereof to demonstrate the improved anti-friction characteristics of the polymer compositions of the invention is a hemostasis valve. The valve may be reliably used with a wide variety of diameters for an inserting device, up to about 9 F (3 mm) catheters and down to guidewires of about 0.014 in. (0.35 mm). A hollow tube can also be used, as in a molded 8 F introducer that can also be used as a catheter for various purposes.

ILLUSTRATIVE EXAMPLES

Together with a mixture comprised of the appropriate tubing or gasket body materials, a combination of the silicone elastomer and lubricant, such as PFPE, is placed in a previously-heated mold and is then heated to a temperature of about 130 to 200 degrees C., preferably at a molding clamping pressure of about 0.5 to 25 MPa, and preferably for a processing time of about 1 to 20 minutes, to obtain the finished product. The silicone rubber or elastomer selected may be one with a particular Durometer hardness (for example, the "Shore A scale" which, for the purposes of this invention, includes similar or any comparable hardness scale for polymer compositions as known in the art). For example, anywhere between about 10 durometer to about 90 durometer can be used. The combined elastomer/lubricant polymers can then be evaluated on certain valve body designs having differing diameters. Insertion force measurements and leakage can then be conducted. An optimal polymer combination can be thus selected for any particular combination of medical device parts or elements, such as a catheter and hemostasis valve, valves or gaskets and various introducers, such as steerable introducers or Swartze introducers, and similar parts of functional parts of medical and biological devices. Usually, the insertion force is desired to be low and no leakage present.

The components of the polymer composition can also be varied to optimize hardness, weight, and thickness, and one skilled in the art is familiar with selecting silicone elastomers, for example, that can result in a final product having a desirable or optimal ranges for any or all of these characteristics. In one embodiment, any of the Elastosil or Silastic series of liquid silicone rubber can be selected. The methylvinyl silicone resin Silastic Q7-4735 is used in the examples below, but many other resins can be selected and similarly used, as noted above, including Silastic Q7-4720.

Example 1

A silicone elastomer resin based upon methylvinyl silicone (Silastic Q7-4735) is selected as the polymer matrix. A liquid lubricant, PFPE synthetic oil, is used at 5 parts per hundred of rubber (phr). The components are mixed using a two-roller mill. The resulting compound is transfer-molded into the gaskets of a hemostasis valve, as noted above, and then post-cured at 150 degrees C. for 2 hours.

Example 2

The same polymer resin as Example 1, but a liquid lubricant (PFPE synthetic oil) is used at 10 phr.

Example 3

The same polymer resin as Example 1, but a solid lubricant (low molecular weight PTFE micropowder) is used at 3 phr, and a liquid lubricant (PFPE synthetic oil) is used at 5 phr.

Example 4

The same polymer resin as Example 1, but a solid lubricant (low molecular weight PTFE micropowder) is used at 8 phr, and a liquid lubricant (polyfluoroalkylether synthetic oil) is used at 8 phr.

Example 5

The same polymer resin as Example 1, but a solid lubricant (boron nitride micropowder) is used at 5 phr, and a liquid lubricant (polyfluoroalkylether synthetic oil) is used at 10 phr.

Example 6

A thermoplastic silicone elastomer, Geniomer 200, is selected as the resin, a solid lubricant (low molecular weight PTFE micropowder) is used at 3 phr, and a liquid lubricant (polyfluoroalkyl ether synthetic oil) is used at 8 phr. The ingredients are mixed into a self-lubricating polymer composition using a solvent or melt compound approach, as known in the art. The resulting composition is then injection molded into a hemostasis gasket as noted above.

Example 7

The utility of the self-lubricating polymer compositions and the parts or elements made from them can be tested under cyclic insertion conditions at constant forces. Unlike currently available products, the insertion forces are very stable at about 0.25 lbs during one hundred insertion cycles, even when five different 6F catheters are used. In comparison, the insertion forces vary from 0.1 to 0.6 lbs during the parallel tests using currently available materials.

Figure 4:
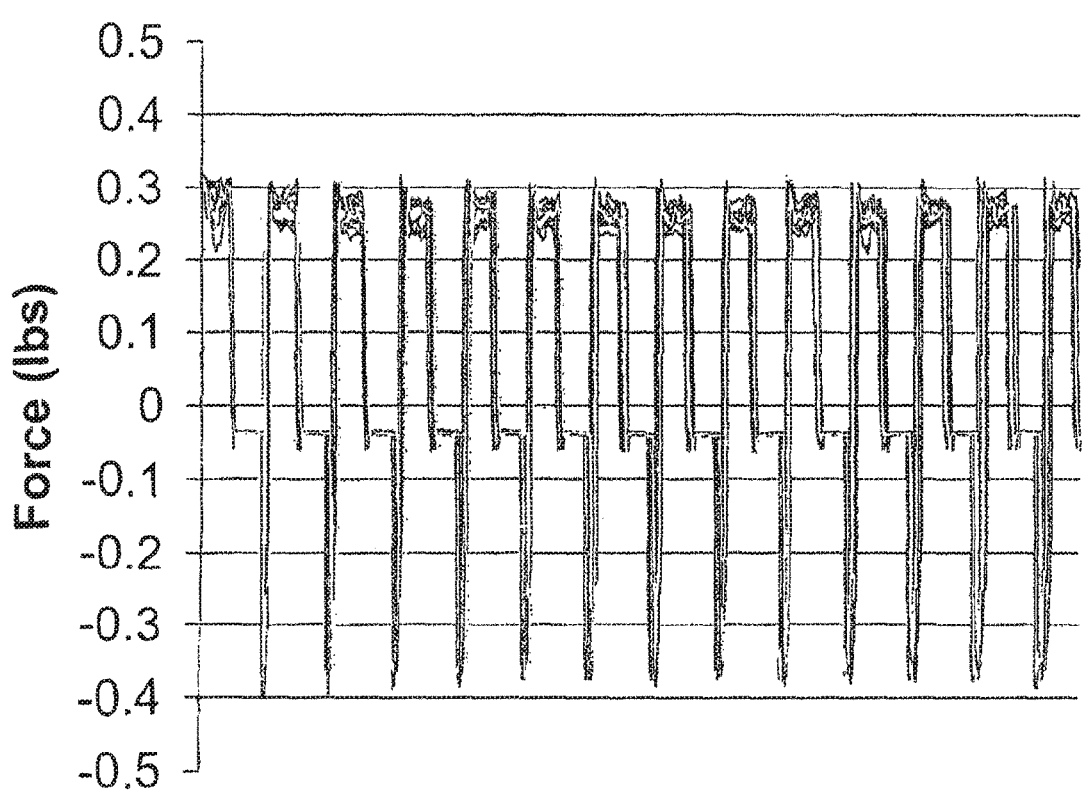
FIG. 4 shows exemplary results of an insertion and withdrawal cycle performed on a hemostasis valve produced from the formulation in Example 1. Each spike represents the forces measured in one of fourteen insertion/withdrawal cycles, and the ten separate lines represent one of ten different catheters inserted into the same hemostasis valve. Even after the unusually large number of insertions and withdrawals for a single hemostasis valve, the forces through each cycle are maintained at an acceptable level, at about 0.3 lbs on average, and within an advantageously small variance in the range of measured force.
Figure 5:
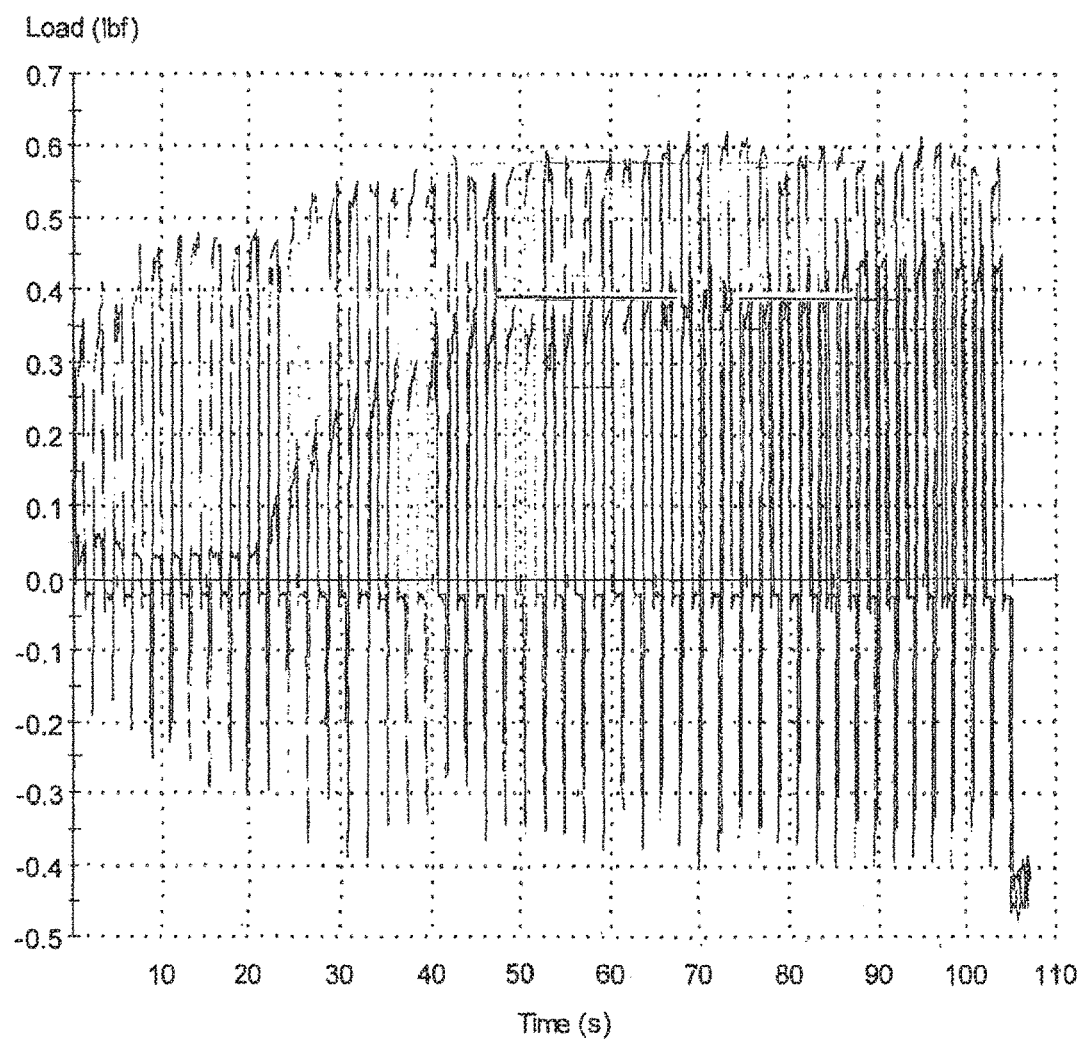
FIG. 5 shows the results of 96 insertion/withdrawal cycles of two different catheters through a conventional hemostasis valve made of unmodified silicone elastomers with external lubricating oil as typically used. The increasing forces after about ten insertion/withdrawal cycles is the result of lubricating oils being removed or wiped off the contacting surfaces. The changes in forces, from about 0.05 lbs to about 0.6 lbs, represent dramatically different forces that would be required to insert and withdraw. Except for cycles 4-10, the forces vary from nearly every cycle to the next.

As shown in FIG. 4, the repeated insertion and withdrawal cycles of the self-lubricating polymer of Example 1 show very little changes in forces measured over the 14 cycles. Even when new catheters are used on the same hemostasis gasket, the forces remain constant. Thus, the self-lubricating polymers of the invention allow a greatly improved consistency in the insertion and withdrawal processes. Comparing to the FIG. 5 results of a conventional polymer and hemostasis gasket, the forces vary over the entire period of the experiment and there is a dramatic and fairly constant increase in required forces at about cycle 10, presumably when the externally applied lubricant is no longer effective.

The reduction in friction forces can be demonstrated in a method that is illustrated in FIG. 1, in which a catheter is inserted into the blood vessel through an introducer that has a hemostasis value contained in its hub. The lubricant releasing from the self-lubricating polymer composition of the hemostasis valve effectively self-lubricates the contact surfaces between the catheter and hemostasis valve, leading to the reduction in the friction forces and/or substantially constant and predictable friction forces.

Although various embodiments of this invention have been described above with a certain degree of particularity, or with reference to one or more individual embodiments, those skilled in the art could make numerous alterations to the disclosed embodiments without departing from the spirit or scope of this invention. It is intended that all matter contained in the above description and shown in the accompanying drawings shall be interpreted as illustrative only of particular embodiments and not limiting. All directional references (e.g., proximal, distal, upper, lower, upward, downward, left, right, lateral, front, back, top, bottom, above, below, vertical, horizontal, clockwise, and counter-clockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the basic elements of the invention as defined in the following claims. The invention is not limited to any particular embodiment or example given here. Instead, one of skill in the art can use the information and concepts described to devise many other embodiments beyond those given specifically here.

What is claimed is:

1. A catheter comprising:
   an inner surface and an outer surface, wherein the outer surface comprises a biocompatible self-lubricating polymer composition, wherein the biocompatible self-lubricating polymer composition consists essentially of:
   a polymer matrix of dimethyl and methylvinyl siloxane copolymers, wherein the polymer matrix is selected from the group consisting of: (a) a polymer matrix, measured as in-mold cured for 10 minutes at 116° C., that has a specific gravity of 1.11, a durometer of 22 in Shore A hardness scale, and a tensile strength of 1347 psi and (b) a polymer matrix, measured as in-mold cured for 10 minutes at 116° C., that has a specific gravity of 1.12, a durometer of 35 in Shore A hardness scale, and a tensile strength of 1427 psi, and about 1 to about 20 phr of a biocompatible lubricant composition comprising a polyfluoropolyether (PFPE) synthetic oil, and one or more of a low molecular weight polytetrafluoroethylene powder, a titanium dioxide micropowder, a molybdenum disulfide micropowder, a graphite micropowder, a baron nitride micropowder, and a porous micropowder, wherein the biocompatible lubricant migrates through the polymer matrix during the use of the biocompatible self-lubricating polymer composition, and wherein the biocompatible self-lubricating polymer composition maintains consistent surface lubricity when exposed to frictional forces.

2. The catheter of claim 1, wherein the PFPE synthetic oil is present at about 4 to about 10 phr.

3. The catheter of claim 2, wherein the PFPE synthetic oil is present at about 4 to about 6 phr.

4. The catheter of claim 1, wherein the lubricant composition consists essentially of PFPE synthetic oil.

5. The catheter of claim 4, wherein the PFPE synthetic oil is present at about 1 to about 10 phr.

6. The catheter of claim 5, wherein the PFPE synthetic oil is present at about 4 to 10 phr.

7. The catheter of claim 1, wherein the polymer matrix of dimethyl and methylvinyl siloxane copolymer is a thermosetting or thermoplastic siloxane copolymer.

* * * * *